United States Patent
Vogt et al.

(10) Patent No.: US 8,409,227 B2
(45) Date of Patent: Apr. 2, 2013

(54) NEURAL IMPLANT

(75) Inventors: Peter Vogt, Hannover (DE); Christina Allmeling, Peine (DE); Kerstin Reimers, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 704 days.

(21) Appl. No.: 11/991,483

(22) PCT Filed: Sep. 6, 2006

(86) PCT No.: PCT/EP2006/066049
§ 371 (c)(1),
(2), (4) Date: Mar. 24, 2008

(87) PCT Pub. No.: WO2007/028801
PCT Pub. Date: Mar. 15, 2007

(65) Prior Publication Data
US 2008/0281420 A1 Nov. 13, 2008

(30) Foreign Application Priority Data
Sep. 6, 2005 (DE) .......................... 10 2005 042 455

(51) Int. Cl.
*A61B 17/08* (2006.01)
(52) U.S. Cl. .................. 606/152; 623/23.72; 623/23.76; 424/423
(58) Field of Classification Search .................. 606/151, 606/152, 154, 155; 623/11.11, 1.13, 1.23, 623/23.64, 23.71, 23.72, 23.75, 23.76; 424/422–426; 530/353
See application file for complete search history.

(56) References Cited

U.S. PATENT DOCUMENTS

| | | | | |
|---|---|---|---|---|
| 5,019,087 | A * | 5/1991 | Nichols | 606/152 |
| 5,656,605 | A * | 8/1997 | Hansson et al. | 424/422 |
| 5,756,457 | A * | 5/1998 | Wang et al. | 424/422 |
| 5,925,053 | A * | 7/1999 | Hadlock et al. | 606/152 |
| 6,436,129 | B1 * | 8/2002 | Sharkey et al. | 607/96 |
| 6,716,225 | B2 * | 4/2004 | Li et al. | 606/152 |
| 7,198,799 | B2 * | 4/2007 | Mueller et al. | 424/426 |
| 7,775,965 | B2 * | 8/2010 | McFetridge | 600/36 |

(Continued)

FOREIGN PATENT DOCUMENTS

| | | |
|---|---|---|
| EP | 1 084 686 | 3/2001 |
| WO | WO 2005/094911 | 10/2005 |

(Continued)

OTHER PUBLICATIONS

Christina Allmeling, Andreas Jokuszies, Kerstein Reimers, Susanne Kall, Peter M. Vogt, "Use of Spider Silk Fibres as an Innovative Material in a Biocompatible Artificial Nerve Conduit", *J. Cell. Mol. Med.*, vol. 10, No. 3, 2006, pp. 770-777.

(Continued)

*Primary Examiner* — Corrine M McDermott
*Assistant Examiner* — Todd J Scherbel
(74) *Attorney, Agent, or Firm* — Greer, Burns & Crain Ltd.

(57) ABSTRACT

The invention relates to a biocompatible neural implant for bridging interruptions or defects in nerves resulting from injuries sustained in an accident or following surgery. Inventive neural implants comprise fibers made from natural or synthetic spider silk and allow interrupted nerves to regenerate across defects such that functional nerve conduction is made possible within a short period of time.

3 Claims, 1 Drawing Sheet

U.S. PATENT DOCUMENTS

Figure 1:
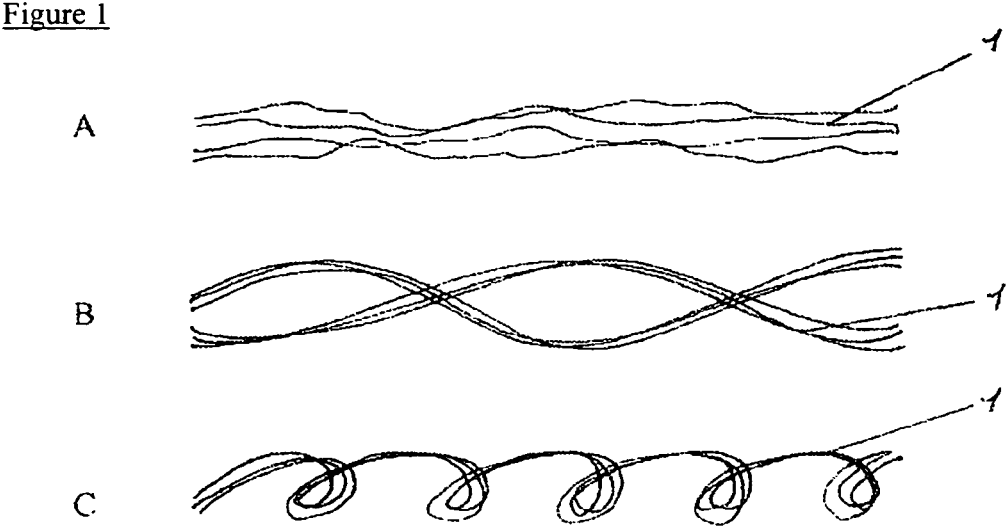

| | | | |
|---|---|---|---|
| 8,106,014 B2 * | 1/2012 | Priestley et al. | 514/17.7 |
| 2001/0053931 A1 | 12/2001 | Hess et al. | |
| 2002/0168338 A1 * | 11/2002 | Baird | 424/93.2 |
| 2003/0100108 A1 * | 5/2003 | Altman et al. | 435/395 |
| 2004/0102793 A1 * | 5/2004 | Yaszemski et al. | 606/152 |
| 2005/0013844 A1 * | 1/2005 | Hadlock et al. | 424/426 |
| 2005/0260706 A1 * | 11/2005 | Kaplan et al. | 435/69.1 |
| 2006/0282173 A1 * | 12/2006 | McFetridge | 623/23.72 |
| 2007/0087024 A1 * | 4/2007 | Knight | 424/423 |
| 2007/0113355 A1 * | 5/2007 | Knight | 8/127 |
| 2008/0249639 A1 * | 10/2008 | Gu et al. | 623/23.76 |
| 2008/0274155 A1 * | 11/2008 | Barton et al. | 424/422 |
| 2010/0222863 A1 * | 9/2010 | Gravett et al. | 623/1.13 |
| 2010/0256756 A1 * | 10/2010 | Altman et al. | 623/13.2 |
| 2012/0023677 A9 * | 2/2012 | Knight | 8/127 |

FOREIGN PATENT DOCUMENTS

WO    WO 2006/030182    3/2006

OTHER PUBLICATIONS

WO 2007/028801, Translation of International Search Report including official preliminary opinion on patenability, Apr. 17, 2008.

* cited by examiner

NEURAL IMPLANT

The present invention relates to a biocompatible neural implant for bridging interruptions or defects in nerves resulting for example from injuries due to an accident or after surgery. Neural implants according to the invention are suitable for inducing regeneration of interrupted nerves even across defects, so that functional stimulus conduction is possible also across the defect bridged by the neural implant within a short period of time.

PRIOR ART

To-date, there have been attempts to assist in regeneration of interruptions in nerves or defects within nerves, where the severed nerve endings cannot readily be rejoined by bridging the defect with an autologous nerve segment originating from a peripheral nerve, for example.

In addition, it is known that peripheral nerve damages can be treated by bridging the defects with an inserted autologous venule or a collagen tubule.

In addition, it is known from EP 1 523 999 A1 that greater mechanical strength can be imparted to endovascular transplants, so-called stents, by including a content of spider silk.

WO 01/56626 describes the use of spider silk only as a suture material but not as an implant for bridging interruptions in nerves.

WO 2005/094911, which was published after the priority date of the present application and therefore is relevant to the state of the art only with respect to novelty, describes composite materials for production of implants, including sheathing, to be used for regeneration of nerves. WO 2005/094911 does not mention that even pure spider silk alone is capable of inducing nerve cells to grow across defects, but instead it describes a number of alternative composite materials from which implants having a stable shape can be manufactured.

US 2003/0100108 A1 describes the production of tendon implants on a matrix which also includes spider silk fibers. With these tendon implants, the mechanical properties of silk fibers are utilized, but their suitability for use in inducing nerves to grow across defects is not utilized in that patent.

DE 100 53 611 A1 describes a guide tube in which axons are to grow. This guide tube, also referred to as a guide rail, consists of polymerized hydroxycarboxylic acids in which synthetic monofilaments produced by extrusion may be arranged.

OBJECT OF THE INVENTION

In view of the known transplants for bridging defects in nerves, one object of the present invention is to provide an alternative to autologous transplants or composite materials. One special object of the present invention is to provide a neural implant having improved properties with regard to restoring stimulus conduction and regeneration of the interrupted nerve. Another object is to provide a neural implant that neither requires nor comprises autologous nerves and, particularly preferably, neither requires nor comprises other autologous tissue.

An object of the present invention is to provide a neural implant for use in the production of a pharmaceutical composition with which defects within nerves can be bridged, such that by using this implant, preferably only one surgical treatment is sufficient to enable regeneration of the nerve for functional stimulus conduction and, particularly preferably, additionally for the growth of natural neural tissue over the area of the defect.

GENERAL DESCRIPTION OF THE INVENTION

To achieve the aforementioned objects, the present invention provides a neural implant comprising spider silk. In particular, the present invention makes available spider silk for use for the production of a pharmaceutical composition whose medical indication is defects in nerves that are to be bridged.

In a first embodiment, the neural implant consists of a fiber, preferably of a plurality of fibers of natural spider silk that are to be arranged between the nerve endings bordering a defect within the nerve. The fibers of spider silk are aligned in such a way that they bridge the distance of the defect in the nerve over which regenerated neural tissue is desired.

In a second embodiment, the inventive neural implant is formed by spider silk fibers arranged within a tubular sheath. As such sheathing to accommodate the fibers of spider silk, collagen tubes are suitable but autologous venules, xenologous acellularized venules or immunologically compatible venules are preferable.

In a third embodiment, the present invention provides a neural implant that already comprises autologous nerve cells, preferably Schwann cells. In this embodiment, the neural implant has a tubular sheathing which has a sheathing according to the second embodiment, in the inside of which there are contained longitudinally positioned fibers of spider silk but wherein remaining cavities between the sheathing and the spider silk fibers are filled with a biocompatible matrix material, e.g., Matrigel (available from Becton Dickinson, extract of the Engelbreth-Holm-Swarm (EHS) sarcoma of the mouse, a tumor containing ECM proteins; the main ingredient is laminin, followed by collagen IV, heparan sulfate proteoglycans, entactin and nidogen).

In a further form of the third embodiment, instead of matrix material alone, a mixture of matrix material with Schwann cells cultured in vitro is used, preferably cultured autologous Schwann cells or cultured immunocompatible Schwann cells. However, it is a disadvantage of this embodiment that prior surgical removal of nerve tissue is necessary to obtain the cultured Schwann cells as well as cultivation of the Schwann cells removed. Therefore, before availability of a neural implant according to the invention, a surgical procedure for obtaining nerve tissue, e.g., peripheral nerves, and a culturing phase is necessary for generating the required number of cultured Schwann cells.

In a fourth embodiment, the neural implant according to the invention is formed from fibers of spider silk arranged around a carrier element. The carrier element can be a plurality of pieces of spider silk fibers arranged in parallel, autologous or acellularized venules as well as strip-shaped elements from the wall of autologous or acellularized venules can be utilized as well as strip-shaped synthetic materials, e.g. surgical suture material.

The embodiments of the neural implant according to the invention are suitable for restoring functional stimulus conduction within a short period of time after being introduced surgically into an interruption or defect in nerves, while also causing the formation of natural nerve tissue across the interruption and defect, respectively. Accordingly, the embodiments according to the invention may be used for the production of a material for medical use for the treatment of defects in nerves, so that the defects are bridged by directional growth of nerve tissue.

It can thus been shown that in bridging defects in motor nerves of mammals over a distance of 2 cm to 4.5 cm or more, stimulus conduction can be restored at least in part and the functionality of the nerve across its interruption or defect, respectively, is essentially restored, preferably completely, within less than a few hours up to two to five days. Within a period of two to ten days, preferably three to four days, in the location of the interruption or defect in the nerve occupied by the neural implant according to the invention has been implanted, the regeneration of nerve tissue can be detected which preferably does not reveal any histological differences in comparison with natural nerve tissue.

On the basis of the observation that the neural implant according to the invention in at least some nerves and implant recipients, respectively, is capable of enabling at least partial stimulus conduction across defects in nerves even without the growth of nerve cells in an implant recipient, it is currently assumed that the fibers of spider silk contained in the neural implant are at least partially capable of conducting electric nerve pulses after implantation in the interruption or defect, respectively, in a nerve.

A particular advantage of the inventive neural implants is that the regeneration of nerves across the interruption and defect, respectively, therein, is accomplished within short period of time. As a consequence of this rapid regeneration of interrupted nerves, it can be established that there is no significant histologically detectable degeneration of the tissue surrounding the interruption or defect, respectively, of the nerve.

A particular advantage of the neural implants according to the invention lies in that within a few days to a few weeks, the ends connected to the inventive implant according to the invention and bordering an interruption and defect, respectively, in nerves, have new tissue that cannot be differentiated histologically from natural nerve tissue in the area of the neural implant and the defect is preferably also bridged by Schwann cells.

Thus, after implantation of neural implants according to the invention in defects in motor nerves, it is observed that axons severed by an accident or surgery are replaced by growth of newly sprouting axons and a rapid reconstruction of natural nerve tissue takes place across the neural implant in the area of the defect.

Another advantage of the neural implants according to the invention is that the spider silk fibers that are considered essential for their function can be obtained in sufficient quantity in sterile form from spiders, preferably kept under sterile conditions, and is available directly for use in an inventive neural implant.

For the purposes of the present invention, the term spider silk and fibers of spider silk, respectively, is preferably understood to refer to the spider silk obtainable from golden orb-weaver spiders, e.g., of the *Nephila* genus, in particular *Nephila clavipes*. In addition, although less preferred, for the purposes of the present invention, the term spider silk may be interpreted as including modified spider silk, e.g., spider silk treated physically by cooling and/or heating, stretching or irradiating, or chemically modified spider silk as well as fibers obtained biotechnologically from spider silk proteins produced in microorganisms, plants or insects. In addition, for the purposes of the present invention, the term spider silk also includes protein fibers produced by other insects, e.g., protein fibers obtainable from butterfly caterpillars, in particular of silkworms or moths.

If necessary, the spider silk may be sterilized, preferably by γ-radiation, for use according to the invention in a neural implant.

DETAILED DESCRIPTION OF THE INVENTION

Inventive neural implants are used for bridging interruptions or defects in nerves, including motor nerves, e.g., the ischiatic nerve or the brachial plexus or sensory nerves, such as the optic nerve and the auditory nerve as well as in vegetative nerves. These neural implants may be used in mammals in particular, preferably in humans.

To do so, in a surgical procedure, neural implants according to the invention are connected to nerve endings of a first end of an interruption or defect in the nerve with a first end of the spider silk fiber contained therein, and a second end of the spider silk fiber contained in the neural implant is connected to the opposing second nerve ending of the interruption, or defect, respectively, in the nerve. The connection between the neural implant according to the invention and the nerve endings that border the interruption or defect is made by a spatially close arrangement of the first nerve ending and the first end of the neural implant, i.e., the spider silk fiber contained therein, as well as a spatially close arrangement of the second nerve ending with the second end of the neural implant, i.e., the spider silk fiber contained therein.

The spatially close arrangement is preferably secured by sewing, e.g., using a known surgical suture material, or gluing, e.g., using a known fibrin adhesive.

In the first embodiment of the invention in which the inventive neural implant only consists of thread-like spider silk, a spatially close arrangement is to be established surgically, preferably by securing each one of the nerve endings that border the interruption or defect in the nerve to one end of the neural implant. In the embodiments of the neural implant according to the invention in which thread-like spider silk is arranged inside a sheathing, preferably an autologous or acellularized venule, as an alternative to direct spatial arrangement, optionally in combination with securing the spider silk on the nerve endings, it is also possible to insert by sections the interrupted nerve endings that are to be joined together into the open end of the sheathing of the neural implant and to secure it there, e.g. by binding or sewing or gluing one nerve ending to one end of the sheathing of the neural implant.

In a preferred embodiment, the thread-like spider silk is contained in the neural implant in the form of one, preferably 10 to 10,000, more preferably 100 to 1000 parallel sections of thread-like spider silk fibers.

Alternatively, however, it is also possible for the thread-like spider silk to be converted to a different structure within the neural implant, e.g. by twisting it, wrapping several bundles of thread-like spider silk around one another, e.g. braiding the spider silk in bundles or wrapping the spider silk fibers around a carrier element in one or more layers in the same direction or in opposite directions. Therein, a neural implant according to the invention may be designed according to the fourth embodiment or may have a carrier element as a supplement in the second or third embodiment, so that this is also arranged inside the sheathing. An autologous or acellular venule or a pin-shaped or strip-shaped wall section of such an autologous or acellular venule may be used as the carrier element of thread-like spider silk or surgical suture material or a pin-shaped or strip-shaped biocompatible material.

Figure 2:
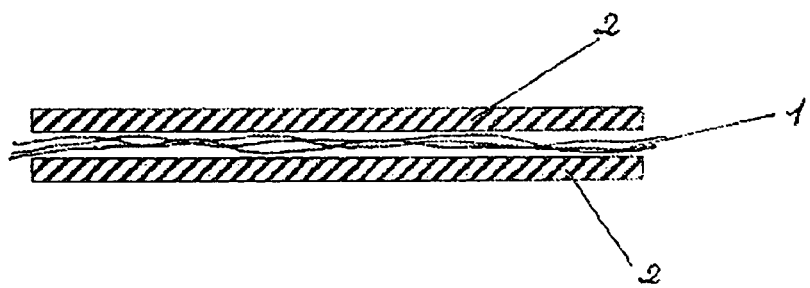
Figure 3:
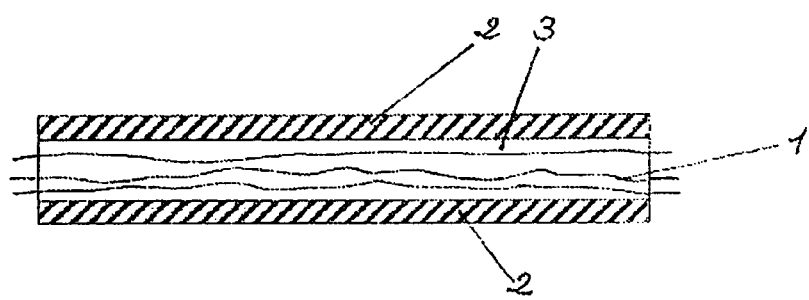
Figure 4:
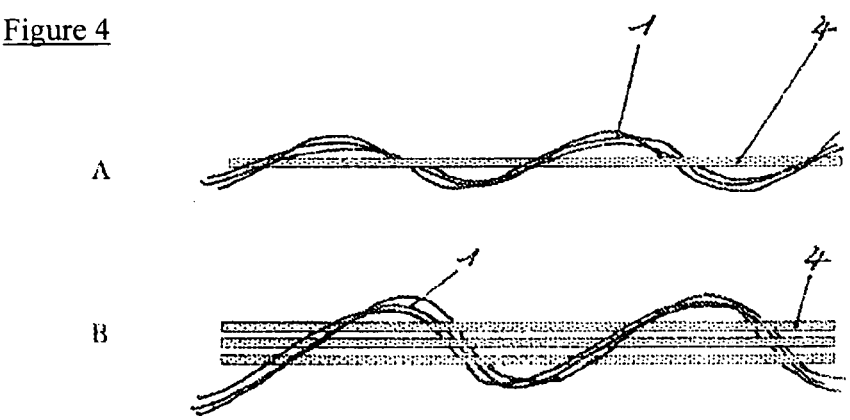

The present invention will now be described in greater detail with reference to the figures, in which FIGS. 1A-1C show a schematic representation of the first embodiment of a neural implant according to the invention, FIG. 2 shows a schematic representation of the second embodiment of a neural implant according to the invention, FIG. 3 shows a schematic representation of the third embodiment of a neural implant according to the invention, and FIG. 4 shows a schematic representation of the fourth embodiment of a neural implant according to the invention.

FIG. 1 shows schematically arrangements of thread-like spider silk in neural implants according to the invention, namely in A) essentially parallel arranged sections of spider silk 1, in B) bundles of thread-like spider silk 1 wrapped around one another, and in C) a bundle of thread-like spider silk 1 twisted around itself.

It is assumed that the thread-like spider silk acts as a directional cord and conductor, respectively, for the growth of nerve cells, in particular of Schwann cells so that the nerve cells align and orient themselves thereon to bridge the interruption, and the defect, respectively, between two separated nerve endings.

FIG. 2 is the second embodiment of inventive neural implants, shown schematically in cross section, in which the thread-like spider silk 1 is arranged within a sheathing 2, preferably essentially parallel to the longitudinal axis of the sheathing 2.

In a refinement of the second embodiment, FIG. 3 shows the third embodiment of the neural implants according to the invention schematically, in which thread-like spider silk I is arranged essentially in the longitudinal direction inside a sheathing 2, with the remaining interspace between the spider silk 1 and the inner surface of the sheathing being completed by a biocompatible material 3, optionally in admixture with autologous or immunologically compatible cultured nerve cells, preferably Schwann cells.

FIG. 4 shows possible variants of the fourth embodiment of the neural implants according to the invention having a carrier element 4 around which the thread-like spider silk I is arranged, e.g. wrapped in a bundle around the carrier element 4 or wrapped in several bundles around the carrier element 4 in the same or opposite directions. The carrier element 4 is preferably a strip taken from an autologous venule or a strip of an acellularized venule, alternatively made of biocompatible material, e.g. surgical material. FIG. 4B shows that the carrier element 4 may also consist of thread-like spider silk 1 or of a mixture of surgical suture material and spider silk fibers.

EXAMPLE 1

Production Of Spider Silk

As an example of spider silk suitable for use in an neural implant according to the invention, a female of the species *Nephila clavipes* was secured with adhesive tape on a substrate. After mechanical irritation of the spinning gland, the secreted fiber of spider silk was obtained, which for the purpose of experiments was wrapped around a sterile 50 mL Falcon tube in a clean bench. To do so, the Falcon tube was rotated at a rotational speed of 5 to 20 rpm.

For the following analyses and examples, natural thread-like spider silk obtained in this manner was used without further treatment or sterilization.

EXAMPLE 2

Bridging A Defect With A Distance Of 2.5 cm In The Ischiatic Nerve

As an example of a motor nerve with a defect, a portion of the ischiatic nerve was removed surgically from the left rear leg of rats for a distance of 2.5 cm. During the same operation under sterile conditions, the defects in various animals were connected by
1) a bundle of approximately 250 to 350 fibers of spider silk approximately arranged in parallel, each approximately 2.8 cm long, or
2) two bundles of approximately 200 fibers each of spider silk of approximately 3 cm long, wrapped in opposite directions around a strip (1 mm edge length) of acellularized venules.

The spider silk was produced according to Example 1.

Therein, the nerve endings of the ischiatic nerve bordering the defect were arranged opposite the ends of the spider silk of the neural implant and fixed to one another alternatively
a) by wrapping the ends abutting head-to-head with spider silk,
b) by sewing using surgical suture material or
c) by bonding with fibrin adhesive.

It has been observed that after waking up from the anesthesia, the rats would not hold the left rear paw unnaturally in a claw shape, as is otherwise customary when there is an interruption in the ischiatic nerve but instead they would use their paw in the natural open position. The animals on which the surgery was performed were able to move their left rear leg naturally and without any significant impairment after only two to four days without requiring additional surgery.

In histological examination of the neural implant five to ten days after implantation it was found that nerve tissue had developed in the area of the interruption in the nerve that had been bridged by the neural implant according to the invention, and this new nerve tissue did not show any significant histological deviations from the natural nerve tissue.

These neural implants were also used to bridge defects (1, 3, and 5 mm) in the auditory nerve and the optic nerve in the rabbit. Stimulus conduction was observed within two to five or ten days after implantation.

In the case of neural implants having a carrier element according to 2), it was found that the acellularized venule strip had adapted completely to the surrounding tissue. No inflammatory processes were observed in the area of the spider silk.

EXAMPLE 3

Neural Implant With Sheathing

As an example of the second embodiment of the neural implants according to the invention, approximately 800 to 1000 spider silk fibers that had been produced according to Example 1 were cut to a length of approximately 3.5 cm and were drawn essentially axially into an acellularized venule. For the purposes of this invention, a sheathing as a component of a neural implant may also have a longitudinal incision, so that the spider silk can be inserted into the longitudinally severed sheathing. Subsequently, the longitudinal incision in the sheathing can be closed e.g. without any additional means due to the inherent tension of the sheathing material by bringing the cut edges of the longitudinal incision together or by sewing or gluing the longitudinal incision or by wrapping the sheathing, e.g., with a spider silk fiber or surgical suture material.

Acellularized venules or strips of acellularized venules that may be used in the neural implants according to the invention have been produced from peripheral veins. As an example for this leg veins were taken from swine that had been sacrificed for other experimental purposes. The venules had a diameter of approximately 2 to 3 mm and a length of 5 cm. For acellularization, these venules were placed in a trypsin solution (0.05 wt % trypsin, 0.02 wt % EDTA) for 24 hours and incubated with agitation. Subsequently, the trypsin solution was removed, and the venules, which were then cell-free, were purified by incubating with PBS while agitating, and this washing was repeated at least once. Such acellularized venules could be used directly or deep frozen at −80° C. in the meantime.

For joining the neural implant to the nerve endings bordering the defect, the nerve endings were each inserted into one end of the sheathing in such a way that the spider silk arranged therein was dimensioned such that it contacted the nerve endings, preferably head-to-head and end-to-end, respectively. The nerve endings were each sutured to one end of the sheathing for fixation.

Alternative neural implants of this embodiment had a length of the spider silk fibers protruding beyond the ends of the sheathing, e.g. by approximately 3 to 5 mm at each end. Then the nerve endings were joined to the neural implant by holding the sections of the spider silk fibers that were outside of the sheathing against a nerve ending each and by wrapping adjacent ends with spider silk, or by coating with fibrin adhesive.

When using these neural implants in defects in the ischiatic nerve of the rat according to Example 3, distances of approximately 5 cm could be bridged, so that the functionality of the nerve was restored within three to five days after implantation.

According to Example 3, here again no interim claw-like posture of the respective paw was observed. The histological examination here again revealed no significant deviations from natural nerve tissue approximately five to ten days after implantation.

EXAMPLE 4

Neural Implant With Sheathing And Biocompatible Matrix Material

As an example of the third embodiment of neural implants according to the invention, neural implants of acellularized venules with axially arranged spider silk fibers according to Example 3 were filled with Matrigel using a syringe.

Functional tests of these neural implants according to Example 3 led to similar results. It is therefore assumed at the present that a biocompatible matrix material does not result in any significant improvement in the properties of the neural implant.

EXAMPLE 5

Neural Implant With Sheathing And Biocompatible Matrix Material In Mixture With Cultured Autolopous Schwann Cells For production of a neural implant with a sheathing in the interior of which were arranged axially aligned spider silk fibers and whose remaining interior was filled with biocompatible matrix material in mixture with cultured autologous Schwann cells, an acellularized venule prepared according to Example 3 was used, into which a bundle of 200 to 300 parallel fibers of spider silk had been drawn.

For production of cultured autologous Schwann cells, peripheral nerves were used that had been removed surgically, freed of epineurum and perineurum and cut into pieces approximately 1 mm long. These nerve fragments were transferred to a medium (DMEM/F12, 20% fetal calf serum, 1% penistreptomycin) in an uncoated petri dish and incubated for approximately three weeks at 37° C., 5% $CO_2$. The medium was replaced with fresh medium three times a week. If increased sprouting of fibroblasts was observed, the nerve fragments were transferred to new petri dishes and cultured further.

After sprouting of the first Schwann cells, the nerve fragments were incubated overnight at 37° C., 5% $CO_2$ with collagenase I and dispase. The nerve fragments were then cautiously homogenized by repeated passes through a cannula by means of a connected syringe and washed in PBS (physiological phosphate-buffered saline solution). After repeated washing steps with centrifugation in the meantime, the cell suspension was transferred to culture bottles coated with poly-L-lysine and cultured at 37° C., 5% $CO_2$ in M2 medium (melanocyte growth medium, Promocell). This medium inhibits the growth of contaminating fibroblasts, while the Schwann cells could subsequently be used.

Cultured Schwann cells were detached with collagenase I and dispase as described above and washed with PBS. The cell suspension could be stored under refrigeration in the meantime or be used directly. Matrigel (available from Becton Dickinson) as the biocompatible matrix material was cautiously mixed with Schwann cells to yield a cell density of approximately $10^2$ to $10^4$/mL matrix material. This mixture of Schwann cells and matrix material was cautiously pipetted into the sheathing in which the fibers of spider silk had already been arranged axially.

It is preferable here for the acellularized venules and accordingly a homologous venule to be completely filled with matrix material except for the spider silk, so the venule assumes a round circumference.

Neural implants produced in this way were used according to Example 2 to bridge a defect in the ischiatic nerve. Nerve function was also restored within a short period of time namely within two to four days, and the complete dysfunction of the motor nerve which manifests in cramping and holding the innervated limbs in a claw-like posture was also avoided.

Histological examination revealed that essentially natural nerve tissue had been formed at the site of the neural implant.

The invention claimed is:

1. Neural implant for bridging interruptions or defects within a nerve, said neural implant consisting thread-like spider silk arranged essentially in an axial direction within an acellularized venule.

2. Neural implant according to claim 1, wherein the thread-like spider silk is natural spider silk.

3. Neural implant according to claim 2, wherein the natural spider silk is golden silk orb-weaver spider silk.

* * * * *

UNITED STATES PATENT AND TRADEMARK OFFICE
CERTIFICATE OF CORRECTION

PATENT NO. : 8,409,227 B2  
APPLICATION NO. : 11/991483  
DATED : April 2, 2013  
INVENTOR(S) : Peter Vogt et al.

Page 1 of 1

It is certified that error appears in the above-identified patent and that said Letters Patent is hereby corrected as shown below:

In the Claims:

Col. 8, line 48      After "consisting", please insert -- of --.

Claim 1

Signed and Sealed this  
First Day of October, 2013

Teresa Stanek Rea  
*Deputy Director of the United States Patent and Trademark Office*